United States Patent [19]

Rubin

[11] Patent Number: 5,760,008
[45] Date of Patent: Jun. 2, 1998

[54] METHOD AND COMPOSITIONS FOR TREATING MALIGNANT TUMORS AND INHIBITING METASTASES OF MALIGNANT TUMORS

[75] Inventor: David Rubin, San Diego, Calif.

[73] Assignee: CO Enzyme Technology Ltd., San Diego, Calif.

[21] Appl. No.: 666,643

[22] Filed: Jun. 18, 1996

Related U.S. Application Data

[63] Continuation-in-part of Ser. No. 360,352, Dec. 21, 1994, Pat. No. 5,639,737, which is a continuation-in-part of Ser. No. 138,195, Oct. 20, 1993, Pat. No. 5,476,842, which is a continuation-in-part of Ser. No. 787,347, Nov. 4, 1991, abandoned, and a continuation-in-part of Ser. No. 57,666, May 5, 1993, Pat. No. 5,340,803.

[51] Int. Cl.$^6$ ........................................ A61K 31/70
[52] U.S. Cl. ........................ 514/25; 514/23; 514/27; 536/4.1
[58] Field of Search ........................ 514/23, 25, 27; 536/4.1

[56] References Cited

U.S. PATENT DOCUMENTS

| | | | |
|---|---|---|---|
| 4,337,760 | 7/1982 | Rubin | 128/1 R |
| 4,424,348 | 1/1984 | Rubin | 536/179 |
| 4,481,195 | 11/1984 | Rubin | 424/180 |
| 4,584,368 | 4/1986 | Rubin | 536/4.1 |
| 4,812,590 | 3/1989 | Saari | 860/137 |
| 4,895,874 | 1/1990 | Rubin et al. | 514/558 |
| 4,946,830 | 8/1990 | Pulverer et al. | 514/23 |
| 5,005,588 | 4/1991 | Rubin | 128/804 |
| 5,169,858 | 12/1992 | Rubin | 514/365 |
| 5,225,542 | 7/1993 | Cramer et al. | 530/396 |
| 5,239,062 | 8/1993 | Blattler et al. | 530/396 |
| 5,240,914 | 8/1993 | Rubin | 514/23 |
| 5,340,803 | 8/1994 | Rubin | 514/25 |
| 5,395,924 | 3/1995 | Blattler et al. | 530/396 |

OTHER PUBLICATIONS

Lotan et al. *Carbohydrate Research*, vol. 213, pp. 47–57, (1991).
Nakamura et al. *Medical Journal of Kiniki University*, vol. 19(4), pp. 537–551, (1994).
Platt et al. *J. Natl. Cancer Inst.*, vol. 84(6), pp. 438–442, (1992).
Smit et al., *Melanoma Res.*, vol. 2(5-6), pp. 295–304, (1992).
Naish–Byfield et al., *Melanoma Res.*, vol. 1(4), pp. 273–287, (1991).
ASSAF et al., Planta Med., vol. 53(4), pp. 343–345, (1987).
Firon et al., Infect. Immun., vol. 55(2), pp. 472–476, (1987).
Kaneko et al. Chem. Pharm Bull. vol. 25 (9), pp. 2458–2460.
BABA et al. GANN vol. 69, pp. 283,284, (1978).

*Primary Examiner*—John Kight
*Assistant Examiner*—Howard C. Lee
*Attorney, Agent, or Firm*—Browdy and Neimark

[57] ABSTRACT

According to the present invention, a substrate for cytochrome p450 which, after oxidation by cytochrome p450, reacts with thiol groups is conjugated to a saccharide to provide a tumor-specific compound which has low toxicity to normal cells. In one embodiment of the present invention, the saccharide conjugate of the cytochrome p450 substrate is administered in conjunction with a saccharide conjugate of a cytotoxic phenol, which provides a synergistic effect in destroying tumors.

17 Claims, No Drawings

METHOD AND COMPOSITIONS FOR TREATING MALIGNANT TUMORS AND INHIBITING METASTASES OF MALIGNANT TUMORS

This application is a continuation-in-part of Ser. No. 08/360,352, filed Dec. 21, 1994, now U.S. Pat. No. 5,639,737,which is a continuation-in-part of Ser. No. 08/138,195, filed Oct. 20, 1993, now U.S. Pat. No. 5,476,842, which is a continuation-in-part of Ser. No. 07/787,347, filed Nov. 4, 1991, now abandoned and Ser. No. 08/057,666, filed May 5, 1993, now U.S. Pat. No. 5,340,803, the entire contents of all of which are hereby incorporated by reference.

FIELD OF THE INVENTION

The present invention is directed to methods and compositions for treating malignant tumors and other metastatic diseases and for inhibiting the metastases of malignant tumors.

BACKGROUND OF THE INVENTION

One of the greatest problems associated with treatment of cancers is delivery of the cytotoxic agent directly to the tumor or cancer cells without affecting normal cells of the body. Although monoclonal antibodies have been contemplated for use as delivery agents for cytotoxic drugs to treat cancers and to inhibit metastasis of existing cancers, monoclonal antibodies have not lived up to their promise as delivery agents for cytotoxic chemicals. There is such a high density of receptors on the surface of cancer cells, and the monoclonal antibodies are such large compounds, that it is impossible to provide sufficient monoclonal antibodies at the cell surface to effectively destroy the cells. The monoclonal antibodies, in other words, are so large that only a very few can be present at the surface of a cell at any one time.

Some cancer cells exhibit high beta-glucuronidase activity and tyrosinase activity, along with a non-specific oxygenase activity which has been attributed to the cytochrome p450 or so-called mixed mono oxygenase enzyme activity.

Acetaminophen is widely used as an analgesic and an antipyretic. However, if one ingests up to about seven grams a day, the vast majority of the drug is conjugated in the liver with glucuronic acid to form a glucuronide. This glucuronide is readily excreted in the urine, although some is conjugated to sulfate. However, the conjugation capacity of the liver is quite limited, and once the available glucuronic acid is depleted from the liver, a second reaction occurs. This reaction is oxidation catalyzed by cytochrome p450 enzymes to yield N-acetyl benzoquinone imine (NABQI) as follows:

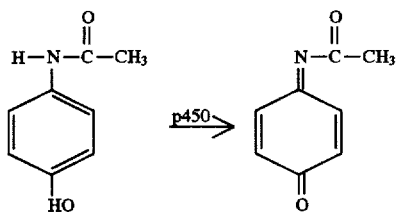

N-acetyl benzoquinone imine is a very toxic material, having an $LD_{50}$ of 20 mg/kg. The body still has a mechanism for detoxification, although this detoxification method is quite "expensive". This detoxification method is referred to in the literature as "suicidal". N-acetyl benzoquinone imine possess a strong affinity for creating a strong covalent bond at site 5 of the ring with sulfhydryl groups of proteins. As long as the affected cell has a reduced glutathione molecule available, the glutathione will effectively commit suicide and will be conjugated to the 5-site of the N-acetyl benzoquinone as follows:

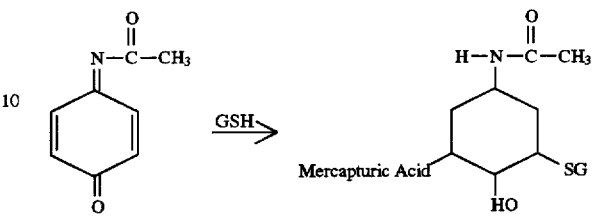

This reaction proceeds until the glutathione molecule is depleted. The N-acetyl benzoquinone imine then conjugates thiol groups of essential proteins, which causes necrosis and eventual death of the cell. Indeed, if one consumed 10 grams of acetaminophen (20 Tylenol® capsules per day), one would die from acute necrosis of the liver.

There have been many reports in the literature relating to the general concept of providing direct transport of an agent which is toxic to tumor cells directly to tumors having β-glucuronidase activity by conjugating the agent with glucuronic acid. Among such reports are Von Ardenne, M. et al., *Agressologie*, 1976, 176(5): 261–264; East German Patent No. 122,386; German Offenlegungsschrift 22 12 014; Sweeney et al., *Cancer Research* 31: 477–478, 1971; Baba et al., *Gann*, 69: 283–284; and Ball, *Biochem. Pharm.* 23: 3171–3177 (1974).

Von Ardenne et al. suggest many types of aglycones which may be conjugated to glucuronic acid and will be active at the tumor site. These include, broadly, alkylating groups, antimetabolites, cytotoxins, membrane-active (lytic) groups, glycolysis stimulators, respiration inhibitors, inorganic and organic acids and cell cycle stoppers. The East German patent cited above also suggests many such combinations, including 5-fluorouracil-glucuronide, aniline mustard-glucuronide, and many others. The Offenlegungsschrift also mentions a large number of glucuronides. Sweeney et al. disclose the anti-tumor activity of mycophenolic acid-β-glucuronides. Bab et al. note the anti-tumor activity of 5-fluorouracil-o-β-D-glucuronide, and Ball discloses the anti-tumor activity of p-hydroxyaniline mustard glucuronide.

Kneen, in European Patent Application 054,924, discloses phenyl ether compounds which can be used to make tumors more sensitive to radiotherapy.

Rubin, in U.S. Pat. Nos. 4,337,760 and 4,481,195, discloses methods for treating tumors having high β-glucuronidase activity with glucuronides with aglycones toxic to the tumor cells with great safety toward the rest of the body by first administering an alkalinizing agent in an amount sufficient to maintain the pH level of non-tumor tissues at approximately 7.5 during the glucuronide treatment to inactivate β-glucuronidase activity in the rest of the body. Thus, the toxic agent is directed only at the cancer cells, as opposed to all of the healthy cells of the body, since the aglycone is only released at the site of the cancer. Tumors having high glucuronidase activity can be identified by assaying tumor cells obtained in a biopsy for β-glucuronidase activity, or by administering a glucuronide whose aglycone has been labelled with a radioactive isotope. If, upon a full body scan, it is found that the radioisotope has accumulated at any specific areas of the body, this will indicate not only the location of the tumor, but the fact that the tumor has sufficient β-glucuronidase activity to deconjugate the glucuronide.

The rationale for the use of 4-hydroxyanisole in the treatment of melanoma is based upon the premise that the only cells in vertebrates that contain tyrosinase are the melanocytes. 4-Hydroxyanisole inhibits DNA synthesis, but by itself shows little toxicity. However, 4-hydroxyanisole is oxidized by tyrosinase to form highly cytotoxic products, and consequently 4-hydroxyanisole is preferentially toxic to those melanoma cells that contain the enzyme tyrosinase [Riley, *Philos. Trans. R. Soc. (Biol.)* 311: 679, 1985]. Morgan et al., in *Clinical Oncology* 7: 227–231, 1981, also note that 4-hydroxyanisole, which is oxidized by tyrosinase, gives rise to cytotoxic oxidation products. The specific melanocytotoxic action of this agent is of particular interest because of its use in treatment of malignant melanoma. It was found that localized malignant melanomas treated by intra-arterial infusion of 4-hydroxyanisole underwent regression, although intravenous administration of the drug was not therapeutically effective. The need to use the intra-arterial route of administration imposes certain limits on the use of 4-hydroxyanisole, since it is not always possible to perfuse the site occupied by a tumor. However, it is believed that, as an adjunct to the conventional treatment of primary melanoma in accessible sites, 4-hydroxyanisole infusion will reduce the dissemination of metastases.

Kanclerz et al., in *Br. J. Cancer* 54: 693–698, 1986, reported that animal studies on experimental melanomas have seen variable results with respect to the therapeutic efficacy of phenolic depigmentation agents. The most active melanocytotoxic agent was found to be an analog of tyrosine, 4-hydroxyanisole. However, evidence for an anti-tumor effect of 4-hydroxyanisole on melanoma in vivo was found to be variable and not conclusive.

Unfortunately, intra-arterial infusion of 4-hydroxyanisole has serious clinical drawbacks, including difficulties in placing and maintaining the patency of intra-arterial catheters. Clogging and/or clotting frequently occur, and, further more, 4-hyroxyanisole has a short half-life in blood, only about nine minutes, after intra-arterial injection.

Saari, in U.S. Pat. No. 4,812,590, discloses that certain carbamates of 4-hydroxyanisole are suitable substitutes for 4-hydroxyanisole in the treatment of melanoma. These carbamates can be delivered by, for example, intravenous injection, and provide increased levels of 4-hydroxyanisole at the tumor site. The delivery of 4-hydroxyanisole is more convenient and safer than many other methods of delivering 4-hydroxyanisole, although, because serum tyrosinase levels may be elevated in patients having tumors with high tyrosinase activity, the metabolic products of 4-hydroxyanisole may be present in locations other than the tumor site.

Pavel et al., *Pigment Cells Research* 2: 241–246, 1989, reported an investigation of the human metabolism of 4-hydroxyanisole using urine samples from melanoma patients treated with 4-hydroxyanisole. The most important metabolite of 4-hydroxyanisole was found to be 3,4-dihydroxyanisole, although other metabolic products included 3-hydroxy-4-methoxyanisole and 4-hydroxy-3-methoxyanisole, as well as quinone. These compounds were excreted predominantly as sulfates and glucuronides. Unfortunately, when tyrosinase oxidizes 4-hydroxyanisole in the body, the product, 4-methoxybenzoquinone, is extremely toxic. Because the 4-hydroxyanisole is not confined to the tumor site, and because the serum level of tyrosinase of patients suffering from tyrosinase-active tumors tends to be elevated, there is always the danger in administering 4-hydroxyanisole to such patients whereby an excess of metabolic products of 4-hydroxyanisole will be present in the blood, and thus exert a cytotoxic effect on cells other than tumor cells.

Chen et al. discovered that serum tyrosinase activity in many persons with metastatic diseases was significantly higher than activity in normal persons. Although the highest serum tyrosinase activity was observed in melanoma and breast carcinoma, there is measurable tyrosinase activity in a variety of other metastatic diseases, including lung carcinoma, colon carcinoma, testicular carcinoma, hepatic carcinoma, pancreatic carcinoma, ovarian carcinoma, leukemia, bronchogenic carcinoma, prostate carcinoma, Hodgkin's disease, and rectal carcinoma, the tyrosinase activity of the foregoing diseases listed in decreasing order.

In addition, serum melanin bands were demonstrated by polyacrylamide disc gel electrophoresis of serum tyrosinase followed by incubation of the gel with L-dopa at room temperature overnight to form melanin bands. The following types of metastatic disease demonstrated serum melanin bands with this technique: mouth carcinoma, multiple myeloma, carcinoma of the stomach, carcinoma of the larynx, carcinoma of the cervix, carcinoma of the tonsil, lymphoma, lymphosarcoma, thyroid carcinoma, carcinoma of cecum, endometrial carcinoma, polycythemia, thymoma, lymphadenopathy, and vertebral carcinoma.

Although the elevation of serum tyrosinase level is explicable in some diseases such as melanoma and breast carcinoma, the high tyrosinase content in melanoma and breast skin increases the tyrosinase circulation level in the blood. Although it has not yet been determined if malignant disease causes a high yield of serum tyrosinase or if a high yield of serum tyrosinase causes malignant disease, it has been postulated that serum immunoglobulins are involved as tyrosinase carriers. Whatever the involvement of tyrosinase in metastatic diseases, there is an elevated level of serum tyrosinase in the case of a great many metastatic diseases.

Passi et al., in *Biochem. J.* 245: 536–542, 1987, compressed the cytotoxicity of a number of phenols in vitro. These researchers found that in vitro, two melanotic human melanoma cell lines, IRE1 and IRE2, and the lymphoma- and leukemia-derived cell lines Raji and K652, exhibited no significant differences in percentage survival among the different cell lines for each drug tested. The major component of toxicity up to 24 hours of di- and tri-phenols was due to toxic oxygen species acting outside the cells, and not to cellular uptake of these phenols per se. It is believed that scavenger enzymes may interfere with the cytotoxic effect of some of these phenols. Additionally, it was noted that the cytotoxic effect of these phenols was not necessarily related to their being substrates for tyrosinase, as the level of toxicity of butylated hydroxyanisole, which is not a substrate of tyrosinase, was significantly higher than that of 4-hydroxyanisole, which is a substrate of tyrosinase.

With respect to dosages of 4-hydroxyanisole to be given, Wallevie et al. report in "Non-Specific Inhibition of In Vitro Growth of Human Melanoma Cells, Fibroblasts and Carcinoma Cells by 4-Hydroxyanisole" in *Hydroxyanisole: Recent Adv. Anti-Melanoma Ther.*, pp. 153–164 (1984) Editor, Patrick A. Riley, that 4- hydroxyanisole was inhibitory to cultures of human melanotic and amelanotic melanoma cell lines, human fibroblasts and a human bladder carcinoma at concentrations of $10^{-3}$ M to $10^{-5}$ M. This activity was independent of tyrosinase activity, as high tyrosinase activity was only connected with the melanotic cell line. Unfortunately, the therapeutic concentration of 4-hydroxyanisole is difficult to obtain in tissue by intra-arterial infusion of the drug. Furthermore, infusion is given only for one hour twice a day, which is an exposure of the cells that in vitro has no inhibitory effect, even at a high concentration of 4-hydroxyanisole.

It has also been found that a genetic aberration in chromosomes 7 and 13 of certain malignant growths expresses itself in a vast biosynthesis of two specific enzymes: β-glucuronidase and tyrosinase. Among these malignant growths are breast cancer, lung cancer, colon caner, melanoma and gastric cancer.

Para-methoxy-phenyl glucuronide (PMPG) damages cancer cells by excessive production of hydrogen peroxide. Hydrogen peroxide oxidizes many amino acid side chains, such as methionine, by transferring one of the oxygen atoms from the hydrogen peroxide to an acceptor molecule, resulting in damage to the cells. However, cancer cells as well as other living cells contain reduced glutathione (GSH). Glutathione, a tripeptide made up of glutamic acid, cysteine, and glycine, in its reduced state as GSH, can react with hydrogen peroxide to mitigate the oxidative damage to cell membranes, as shown in the following equation:

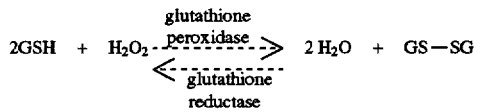

SUMMARY OF THE INVENTION

It is an object of the present invention to overcome the aforementioned deficiencies in the prior art.

It is another object of the present invention to provide a method and composition for treating metastatic cells.

It is another object of the present invention to provide a composition and method for treating metastatic cells without damaging normal cells.

According to the present invention, a compound which is a substrate for cytochrome p450 which, after oxidation by cytochrome p450, reacts with thiol groups is conjugated to a saccharide such as glucuronic acid. This conjugate has a remarkably low toxicity; when acetaminophen is the cytochrome p450 substrate, the saccharide has an $LD_{50}$ of 5200 mg/kg when administered orally in mice, with no sign of liver damage.

For purposes of the present invention, a "substrate for cytochrome p450" means a compound which, when oxidized by cytochrome p450, reacts with at least one thiol group on a compound which has at least one thiol group.

In one embodiment of the present invention, the saccharide of the cytochrome p450 substrate is administered in conjunction with a saccharide conjugate of a cytotoxic phenol, such as paramethoxy phenol glucuronide, or PMPG, which provides a synergistic effect in destroying tumors.

It is believed that this synergistic effect in treating tumors is because cytotoxic phenol is oxidized in the tumor by tyrosinase at the tumor site to form a more cytotoxic compound. In PMPG, this is methoxy ortho benzoquinone. Methoxy ortho benzoquinone produces hydrogen peroxide in the tumor. The glutathione in the tumor has the capacity to some extent to neutralize the oxygen stress resulting from the production of hydrogen peroxide as follows:

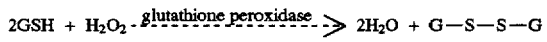

Now the enzyme glutathione reductase has the capacity for reversing this reaction and regenerating reduced glutathione:

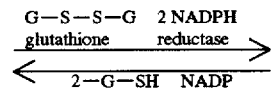

In other words, this is a catalytic reaction, and unless one administers substantial amounts of PMPG, the oxygen damage to the tumor cells can be repaired.

When additional N-acetyl benzoquinone imine is present, this "defense mechanism" of the cells is destroyed, because the N-acetyl benzoquinone imine completely removes the glutathione molecule and the glutathione can no longer serve as a hydrogen donor in a reversible manner. As a result, the tumor cell can no longer stand the oxygen stress caused by the methoxy ortho benzoquinone molecules.

Moreover, the N-acetyl benzoquinone imine can further attack essential sulfhydryl groups in sensitive proteins, and thus increase and facilitate death of the cancer cells. One of these proteins is ornithine decarboxylase. This enzyme regulates the formation of the polyamines spermine and spermidine.

In the unlikely event that an overdose of the conjugate of the cytochrome p450 substrate is administered, an antidote is available. N-acetyl cysteine or glutathione can be administered as an antidote to excess cytochrome p450 substrate. The N-acetyl cysteine or glutathione serves as a hydrogen donor for N-acetyl benzoquinone imine. This prevents generation of excess peroxide, saving the non-cancerous cells from oxygen-induced destruction.

It is well known that in the absence of spermine and spermidine, cells remain at the "Go" stage of mitosis and do not multiply. It is also known that ornithine decarboxylase is one of the shortest-lived enzymes, having a half life of ten minutes. This enzyme has essential sulfhydryl groups that are very easily oxidized to S-S bonds, and thus this growth factor is under control in normal cells. In cancer cells, there are more reducing systems than in normal cells, mainly GSH, glutathione reductase, and glutathione peroxidase, that facilitate the recovery of ornithine decarboxylase. Thus, these reducing systems favor the abundant formation of spermine and spermidine and thus the uncontrolled growth of the cancerous cells.

The combination of PMPG as a cytotoxic phenolic saccharide conjugate and a saccharide conjugate of a cytochrome p450 substrate such as para acetaminophenyl glucuronide, PAPG, operate as follows:

(1) suppuration and removal of glutathione by PAPG
(2) extenuated destruction via oxidation and free radical formation by PMPG
(3) selective co-valent reaction with sulfhydryl sensitive groups of ornithine decarboxylase and thus nonreversible denaturation of the enzymes with consequent removal of spermine and spermidine by PAPG.
(4) further destruction of less sensitive SH groups and peroxidative damage to the nucleic DNA by both PMPG and PAPG causing final cell death.

Of course, one can also use a combination of the glucuronides and/or galactosides of acetaminophen and methoxy ortho benzoquinone.

In another embodiment of the present invention, the glucuronide or saccharide conjugate of the cytochrome p450 substrate is administered together with at least one cytotoxic phenol which is a substrate for tyrosinase which is conjugated to at least one saccharide to provide at least one compound for treating tumors which have both saccharidase activity and tyrosinase activity. The saccharide, upon contact with the saccharidase, is cleaved to produce the tyrosinase substrate cytotoxic phenol at the tumor site, which, upon being acted upon by tyrosinase at the tumor site, then can exert its cytotoxic effect on the tumor cells. In this manner, the truly toxic compound is delivered only to the tumor cells, and there is virtually no contact with the healthy cells, since neither the cytotoxic phenol nor acetaminophen is released at the tumor site until the saccharide compounds have been cleaved by the saccharidase at the tumor site. This avoids contact of healthy cells with the cytochrome p450 substrate and the cytotoxic phenol, and the reaction products of the cytotoxic phenol and any tyrosinase can be limited to the tumor site. By using a plurality of saccharide conjugates, one can obtain a synergistic effect in treating tumors having tyrosinase activity, since the different saccharide molecules of the conjugates act at different sites on the tumor membrane.

The saccharide to be conjugated to the cytochrome p450 substrate is any saccharide that can be conjugated to the substrate and which is readily cleaved by a saccharidase enzyme at a tumor site. Examples of such saccharides include lactose, glucose, galactose, fructose, arabinose, mannose, gulose, ribose, xylose, lyxose, erythrose, maltose, cellobiose, sucrose and rhamnose.

The cytochrome p450 substrates for use in the present invention may be any compound that can be oxidized by a heme iron containing monooxygenase to form a compound that reacts after such oxidation with thiol groups. The cytochrome p450 enzymes catalyze the insertion of an oxygen atom into a carbon-hydrogen bond as follows:

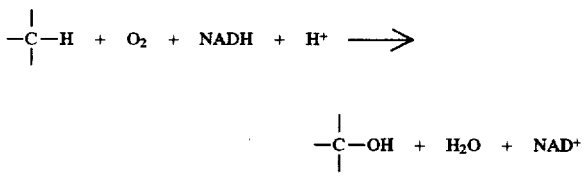

The high reactivity of oxygen that is brought about by its reaction with iron allows these enzymes to catalyze the reaction of oxygen with unreactive groups on compounds which have a carbon-hydrogen bond.

For example, cytochrome p450 enzymes can convert methyl groups into hydroxy-methyl groups.

The p450 enzymes can attach stable molecules through the perferryl ion, $FeO_3^{3+}$, which may be regarded as an oxygen atom that is attached to a ferric ion in the active site of the enzyme. The oxygen in this species is highly reactive and can abstract a hydrogen atom from a substrate.

Among the compounds which are substrates for cytochrome p450 and which, after reaction with cytochrome p450, react with thiol groups, are acetaminophen, glutathione, and ornithine dicarboxylase.

A combination of saccharide conjugates can be used in conjunction with a cytochrome p450 substrate conjugate; such combination can be chosen for use in treating tumors can be chosen to have the maximum effect for the particular tumor treated. For example, melanomas have both α-D-glucosidase activity as well as β-D-glucuronide activity. Therefore, melanomas are treated with a cytochrome p450 substrate conjugate such as acetaminophen along with a saccharide conjugate of α-D-glucoside and a tyrosinase substrate as well as a saccharide conjugate of β-glucuronide with a tyrosinase substrate. In order to prevent metastases, one of the saccharides can be lactose, or lactose can be administered in conjunction with the saccharide conjugates. Mammary tumors, on the other hand, have a very high β-galactosidase activity, and these tumors are effectively treated by conjugating β-D-galactoside to a cytotoxic phenolic compound, which can be used in conjunction with a conjugate of a cytochrome p450 substrate and a conjugate of a cytotoxic phenolic compound with a β-D-glucuronide. One skilled in the art can readily determine what saccharide enzyme or enzymes activity a particular tumor possesses, and tailor the combination of conjugates for optimum destruction of the tumor.

When the saccharide used to make the conjugate is lactose, the cytotoxic drug is used to destroy the receptor sites on the tumor and the lactose part of the conjugate acts to prevent metastasis of the tumor while the cytotoxic portion treats the tumor.

The cytotoxic phenolic compounds which are substrates for tyrosinase compounds which can be used in conjunction with acetaminophen conjugates in the present invention are those which have been found to be toxic to human tumor cells, including tyrosine, 4-hydroxyanisole, butylated hydroxyanisole, L-3,4-dihydroxyphenylalanine, dopamine (3,4-dihydroxyphenethylamine), tertbutylcatechol, hydroquinone, resorcinol, 6-hydroxydopa (3,4,6-trihydroxyphenylalanine), 4-tert-butyl phenol, 4-tert-amyl phenol and 4-benzomethoxy phenol and methyl gallate. These compounds are conjugated to glucuronic acid and/or saccharides by any convenient means to form the compounds of the present invention.

The saccharide other than lactose is any saccharide that can be conjugated to a cytotoxic phenol and which is readily cleaved from the phenol by an enzyme particular to a tumor. Several, nonlimiting, examples of such saccharides include glucose, galactose, fructose, arabinose, mannose, gulose, ribose, xylose, lyxose, erythrose, maltose, cellobiose, sucrose and rhamnose. As noted above, lactose is preferred.

In addition, the cytotoxic phenolic compounds conjugated to the saccharides as well as the conjugates of cytochrome p450 substrates can be used in the acetylated form. That is, when the conjugates are prepared by conjugating a phenolic compound or a cytochrome p450 conjugate with methyl (tri-O-acetyl-α-D-glycosyl bromide)-uronate, a triacetyl methyl ester is formed. This triacetyl methyl ester can be used in the acetylated form. Since these acetyl groups are not easily removed, the compounds are not particularly cytotoxic to normal cells. However, since primitive cells, such as growing cancer cells, can produce many different types of enzymes, including acetylase, these primitive cells can readily remove the acetyl groups on the acetylated conjugates to provide active forms of the compound directly at the site of a growing tumor. Of particular importance are the 3-acetylated conjugates, since the 3-acetylated conjugates are lipid soluble and are retained by the body at the tumor site for a much longer period of time than the unacetylated conjugates. The 3-acetylated conjugates have also been found able to cross the blood-brain barrier.

Of the glucuronide conjugates of the present invention, the glucuronide of 4-hydroxy-anisole (or PMPG, for para-methoxy-phenyl-glucuronide) is a preferred compound for use with acetaminophen conjugates. Because this compound is a glucuronide, it possesses a low toxicity, as an important mechanism of the liver is to detoxify toxins via conjugation with glucuronic acid. This glucuronide conjugate is used with the appropriate glycon conjugate of acetaminophen for treating tumors.

The cytochrome p450 substrate conjugate with glucuronic acid or saccharides can be administered alone or in combination with a glucuronide or saccharide conjugate of a cytotoxic phenol such as PMPG for treating a variety of cancers which exhibit tyrosinase activity. Examples of such cancers are prostate cancer, non-small cell carcinoma, squamous cell carcinoma, breast cancer, ovarian cancer, and brain tumors. The response rate was similar and, in some cases superior, to the results obtained with PMPG.

The dosage was from about 1 to about 10 grams of the glucuronide conjugate and from about 1 to about 10 grams of the acetaminophen conjugate. In treating prostate cancer according to the present invention, the PSA of patients dropped from an average of 400 to a normal range of 0–5 in 85% of the patients within three months of treatment. The optimal dosage for prostate cancer was found to be about 5 grams PMPG and about 3 grams of PMPA.

DETAILED DESCRIPTION OF THE INVENTION

Many saccharides, such as lactose, either alone or conjugated to a cytotoxic drug, are specific for organ cell lectins, and thus can be used either for preventing metastases of malignant tumors and/or for treating primary malignant tumors. The active substances may be administered enterally as well as parenterally, and are metabolized from the organism in a known manner.

A number or methods can be used to manufacture the cytochrome p450 substrate conjugates with saccharides according to the present invention, including those disclosed in Rubin, U.S. Pat. No. 4,481,195 and Rubin, U.S. Pat. No. 4,424,348, the entire contents of both of which are incorporated by reference.

The cytochrome p450 substrate is conjugated to the saccharide by conjugation of the phenol group on the substrate molecule with methyl (tri-O-acetyl-α-D-aglycon bromide) uronate, the active form of the saccharide for conjugation, and may be produced in accordance with the teachings of Bollenback et al., *J. Am. Chem. Soc.* 77: 3310, 1955, the entire contents of which are hereby incorporated by reference.

The substrate for cytochrome p450 is introduced to the methyl (tri-O-acetyl-α-D-aglycon bromide) uronate in a solution of the substrate catalyzed by a small, catalytic amount of silver oxide. Besides phenol, there may be used as a solvent quinoline, methyl nitrile, or methyl cyanide. Silver carbonate may be used as the catalyst in place of silver oxide.

Another method of condensation is to use sodium or potassium hydroxide as the condensing agent in acetone or methanol solution. A stoichiometric excess of the substrate is maintained at room temperature for 72 hours, or until the reaction to form the triacetyl methyl ester is complete.

The triacetyl methyl ester can be used as such or can be converted to the acid form of the conjugate by reaction of the triacetyl methyl ester as obtained above with a ½ molar amount of 0.5N barium hydroxide which is added slowly to this solution to form a white precipitate. Preferably, an excess of barium hydroxide or methanolic sodium hydroxide or sodium methoxide is added until there is no more precipitation.

The addition of 0.5N sulfuric acid, volume to volume, followed by cooling in ice water for 20 minutes, releases the free saccharide.

The mixture is then filtered, and the supernatant is dried in vacuum and crystallized from ether.

The triacetylated form of the saccharide conjugate is the preferred form of the compounds to be used in accordance with the present invention. However, the free acid form of the conjugates may also be used when a water-soluble form of the conjugate is desired. Therefor, whenever the term "saccharide compound" is used in the present specification and claims, it is understood to include not only the free acid form of the conjugate but also the acetylated conjugates as well as pharmaceutically acceptable salts and esters thereof, as discussed hereinabove.

The selectivity of the saccharide compounds toward tumors can be greatly increased and the possible deconjugation of the toxic aglycones in healthy parts of the body can be greatly minimized by administering to the patient, prior to or simultaneously with administration of the conjugate, an alkalinizing agent which will maintain the pH of the rest of the body at a pH of about 7.4. Of course, this alkalinizing agent has minimal effect on the pH of the stomach per se. Of course, this pH does not apply to the gastrointestinal tract, where the pH may vary substantially from about 7. It is well known that the activity of β-glucuronidases is substantially nil at a pH of 7.4. Thus, the administration of alkalinizing agent such as bicarbonates or other basic salts will substantially decrease and eliminate β-glucuronidase activity which occurs naturally in certain healthy tissues such as the kidneys, spleen and liver. Such an administration of alkalinizing agent will not diminish the acidity of the tumor cells themselves, however, in view of the naturally low pH of the tumor cells, the mechanism of prior hyperacidification and the lack of substantial blood perfusion through the tumor area, as well as other mechanisms. It has been suggested in the literature, in fact, that bicarbonate will actually increase the acidity of the cancer cells, cf. Gullino et al. *J.N.C.I.* 34(6): 857–869, 1965.

Since the saccharidase activity of the tumor cells is enhanced by acidification, and the saccharidase activity of the rest of the body, particularly of the kidneys, will be substantially eliminated by alkalinization, the cytochrome p450 substrate and optional cytotoxic phenols will only be released at the tumor site itself due to deconjugation of the saccharides by the action of the saccharidase. Without the alkalinization step, substantial amounts of toxic materials may be released, for example in the kidneys, and the cytotoxic phenols so released may cause substantial damage to these organs if there is any tyrosinase present at this site. Thus, only through the use of the present invention can saccharides of cytochrome p450 substrates and of phenols which are toxic to tumor cells be used with a great degree of safety and efficacy. The greater the toxicity of the phenols after the action of the tyrosinase, the more important is the alkalinization step.

Other steps of increasing saccharidase activity at the tumor cells may also be undertaken. One method of accomplishing this is to elevate the temperature of the toxic cells at the time of treatment. This may be done by elevating the temperature of the entire body such as by the use of a pyrogenic drug or by elevating the temperatures solely in the area of the tumor cells, such as by microwave radiation or electrical current. Raising of the temperature increases saccharidase activity, thereby increasing the efficiency of the deconjugation of the saccharides. It is known that, in the temperature range of about 35° to 45° C., an elevation of temperature of about 3° C. increases saccharidase activity by up to 50%.

Known pyrogenic drugs that can be administered to raise body temperature include etiocholanolone, progesterone, dinitrophenol, dinitrocresol, and the like. Because the acetaminophen, a known antipyretic, is conjugated to a saccharide, the acetaminophen does not act to counteract the pyrogenicity of the pyrogenic drugs until it is released at the tumor site.

Because dinitrophenol and dinitrocresol are also cytotoxic, the use of these compounds is preferred, particularly when they are administered as the saccharide. In this case, when the saccharide is deconjugated at the tumor site, the aglycone will act not only to denature the cytoplasmic protein, but also to raise the temperature directly in the region of the tumor cells, thus greatly increasing the efficiency of further deconjugation.

Local hypothermia in the region of suspected tumor cells is preferred to general hypothermia, because general hypothermia will also increase the saccharidase activity in healthy cells. However, because of the alkalinization step, this is not a major problem. If the hypothermia is local, then this provides an additional degree of certainty that the glucuronides will only become deconjugated at the tumor site. The application of microwave treatment directed at the suspected tumor site is one way to achieve total hypothermia. Due to the different electrical resistance of tumor cells, another method of achieving some degree of local hypothermia is by administering a low electrical current through the body.

A further manner of increasing saccharidase activity selectively at tumor cells is by administration of estrogen to female patients or testosterone to male patients, for tumors which are not estrogen- or testosterone-dependent, respectively. It has been reported that these compounds induce saccharidase activity in trophoblastic cells. Since certain tumor cells are known to be trophoblastic, this method is particularly useful for those types of cells. The alkalinization step prevents damage to healthy trophoblastic cells.

Before treatment of patients in accordance with the present invention, it should be ascertained that the particular type of tumor involved has both a high saccharidase activity as well as a high tyrosinase activity. This may be done in a number of ways.

One way is to assay tumor cells obtained in a biopsy for saccharidase activity. If such a test is positive, then the pharmaceutical compositions of the present invention may be administered. More particularly, by ascertaining the particular saccharidase activity of the tumor cells, one can select the particular saccharide conjugate or mixture of saccharide conjugates which will most effectively treat the tumor cells. By using a conjugate or conjugates which are cleaved by the saccharidases most must abundant in the tumor cells, one can maximize the amount of cytotoxic phenolic compound delivered directly to the tumor site.

A second method is the administration of a saccharide whose aglycone has been labelled with a radioactive isotope. If, upon a full body scan, it is found that the radioisotope has accumulated at any specific areas of the body, then this will indicate not only the location of the tumor but the fact that the tumor has sufficient saccharidase activity to deconjugate the saccharide. After this has been determined, the appropriate amount of the appropriate saccharide conjugate(s) of choice may be administered. If there are no tumors present, or the tumors are of the type which do not have saccharidase activity, then there will be no accumulation of radioisotope in the body as the alkalinization step of the present invention eliminates all saccharidase activity, and the isotope will be passed through the body.

Another method for diagnosing tumors which are treatable by means of the present invention, and to determine which saccharide or saccharides should be used to form the conjugates, is to test for the presence of free glucuronic acid in the urine. While the presence of glucuronides in the urine is common, the presence of free glucuronic acid in the urine, and particularly the presence of increasing amounts of glucuronic acid when tested over a period of several days, is a potent indication of the presence of tumors with $\beta$-glucuronidase activity. It has been hypothesized that the presence of free glucuronic acid in the urine in cancer patients is caused by the action of $\beta$-glucuronidase in the cancer cells on the intercellular filaments and connective tissue. Glucuronic acid is a reaction product of such activity because the intercellular filaments and connective tissues are composed of polymers of which glucuronic acid is an element, and which are a known substrate for the enzyme $\beta$-glucuronidase.

A method for distinguishing free glucuronic acid from conjugated glucuronides in the urine has previously been disclosed in Rubin, U.S. Pat. No. 4,337,760, the entire contents of which are hereby incorporated by reference. Both glucuronides and glucuronic acid give a chromogenic complex with tetraborate in concentrated sulfuric acid which reacts with m-hydroxydiphenyl to create a colored water-soluble complex. When lead acetate is added at an alkaline pH, the glucuronides precipitate and the addition of ditizone (dithiosemicarbazone) makes a stable complex with the excess lead. Accordingly, an optical reading may be taken representative of the amounts of total glucuronides and free glucuronic acid after tetraborate and m-hydroxydiphenyl have been added. A second reading may then be taken after the conjugated glucuronides and excess lead have been removed from the aqueous phase by the addition of basic lead acetate and after ditizone has been added. Alternatively, the conjugated glucuronides can be removed by reaction with barium hydroxide. The addition of barium hydroxide to the urine sample will precipitate the conjugated glucuronides but not the free glucuronic acid. After centrifugation and filtration the deconjugated glucuronides are eliminated and what remains is only the free glucuronic acid. A reading representative of the amount of free glucuronic acid may then be taken. The alternative procedure bypasses the requirement for ditizone.

In the urine test for glucuronidase activity, normal patients exhibit between 200 and 400 mg per 24 hours of free glucuronic acid in the urine. Cancer patients with well developed tumors which have $\beta$-glucuronidase activity show greater than 200 to 7000 mg per 24 hours of free glucuronic acid. Accordingly, using this above test, if more than about 400 mg per 24 hours of free glucuronide is exhibited, this is an excellent indication of the presence of tumors having a high $\beta$-glucuronidase activity.

A negative indication on this urine test will not conclusively rule out the presence of tumors having $\beta$-glucuronidase activity, because tumors in their initial stages, although they might have $\beta$-glucuronidase activity, might not release sufficient free glucuronic acid to cause a positive reading in the urine. Therefore, the urine test should be repeated, and if an increasing amount of free glucuronic acid is found, then this is another indication of the presence of a tumor having $\beta$-glucuronidase activity.

Although 4-hydroxyanisole and other cytotoxic phenols may not generally be toxic to healthy cells, when these substances are acted upon by tyrosinase, they are converted to toxic metabolites which have their dominant effect inside the cells, where they are produced (i.e., melanoma cells and melanocytes), as tyrosinase is known to convert several phenols (e.g., its natural substrate, tyrosine) to catechols and quinones which react strongly with SH groups. In the case of acetaminophen the conversion to N-acetyl benzoquinone-imine is catalyzed by the enzyme cytochrome p450 (LYPIAI) which is abundant in some cancer cells.

Tyrosinase activity of tumor cells can be determined by assaying a sample obtained from a biopsy by the method of Pomerantz, *J. Biol. Chem.* 241: 161, 1966, using L-[3,5-$^3$H]-tyrosine (AmershamTRK 200). Using this method, Wallevik et al. (op. cit.) determined that melanotic melanoma had the greatest tyrosinase activity, while bladder carcinoma and amelanotic melanoma had less but measurable tyrosinase activity. Skin fibroblasts were found to have no tyrosinase activity.

Once it has been determined that the patient has a tumor having both tyrosinase and saccharidase activity, the first step of the treatment is to administer a dose of glucose, such as 100 grams of honey, glucose, or other simple sugar. Before treatment with the conjugates, an intravenous drip is administered of a solution in distilled water containing approximately 10% glucose and 60 millequivalents sodium bicarbonate. Approximately one liter of this solution is administered, assuming no contraindications, and the pH of the urine is checked to determine that it has reached a pH of approximately 7.4. This establishes that the system has become alkalinized and it is now safe to administer the glucuronide. Another liter of the same glucose-bicarbonate solution containing the desired amount of conjugate of acetaminophen with optional conjugates of phenolic tyrosinase substrates is then administered. This administration is repeated daily as needed. It is desirable to maintain high levels of glucose in the blood during treatment according to the present invention, unless the saccharide is glucose, of course. When glucose levels in the blood are increased, they are generally increased at least 180%, and preferably about 250% of normal.

When galactose is the saccharide of choice, exogenous galactose should not be administered to the patient, such as from dairy products. In the same manner, when another saccharide conjugate is administered, the patient should not receive exogenous saccharide so that the saccharidase activity can be centered on the conjugate, and not on exogenous saccharide.

If there are contraindications for the administration of bicarbonate parenterally, then an antacid may be administered orally. This antacid may be any conventional antacid such as sodium bicarbonate, magnesium bicarbonate, aluminum hydroxide, aluminum magnesium silicate, magnesium carbonate, magnesium hydroxide, magnesium oxide, or the like. The important criterion is that the pH of the urine become approximately 7.4 and remain so during treatment.

The hyperacidification of the tumor cells is caused by a hyperglycemic condition in the patient. Therefore, any hyperglycemic agent may be used as the hyperacidification agent, such as, for example, fructose, galactose, lactose, or glucagon. Furthermore, it should be understood that this hyperglycemic condition may be effected in any known manner. For example, if the patient is diabetic, then the condition can be brought about by decreasing the insulin administration. Of course, the hyperacidification agent should not be the same saccharide as in the conjugate to be administered.

Any agent which will raise the pH of the urine to approximately 7.4 can be used as the alkalinizing agent, including sodium or potassium bicarbonate or citrate, or other basic salts or antacids. While it is preferred that these agents be administered intravenously, they may be administered orally.

When the term "approximately 7.4" is used in the present specification and claims, with respect to the pH level to be maintained in the rest of the body, it should be understood that a pH level slightly above or below 7.4 may be used, although this is not preferred. Of course, this pH does not apply to the gastrointestinal tract, where the pH may vary substantially from about 7. As the pH decreases from 7.4, the β-glucuronidase activity increase until the optimal pH is reached. Furthermore, below pH 7.0 the remainder of the body will not be alkaline but will be acid. Above 7.4 the danger of alkalosis increases without any substantial further decrease in β-glucuronidase activity. A pH level of 7.4 is preferred, as this is physiological pH and cannot be harmful to the body; it is known that the β-glucuronidase activity in healthy organs is substantially nil at this pH level.

The dosage of the compounds administered should be monitored to avoid any side effects due to the massive release of toxins caused by the dying cancer cells. It may be preferable to treat the patient with the compounds of the present invention in short courses of several days, leaving several days in between to allow any toxins released by the dying cancer cells to leave the body before continuing with treatment.

When a conjugate of lactose with a cytotoxic agent is administered it must not be administered orally. Intramuscularly is a preferred method of administration, with the lactose dissolved in a suitable carrier, e.g., water. When the lactose is administered as part of a conjugate, the amount to be administered depends upon the particular cytotoxic drugs used. However, one skilled in the art can readily determine the optimum amount of the conjugate to be administered, taking into account the patient's condition, the size of the tumor, etc. For example, using New Drug Exemption Guidelines published by governmental authorities, one skilled in the art can readily establish preclinical and clinical trials for determining the preferred dosages to be used. One skilled in the art would, by use of methods described in standard textbooks, guidelines and regulations as described above, as well as common generally knowledge within the field, be able to select the exact dosage regimen to be implemented for any selected conjugate using merely routine experimentation procedures.

In determining dosages of the conjugates to be administered, the dosage and frequency of administration is selected in relation to the pharmacological properties of the specific conjugate. Normally at least three dosage levels should be used. In toxicity studies in general the highest dose should reach a toxic level but be sublethal for most animals in the group. If possible, the lowest dose should induce a biologically demonstrable effect. These studies should be performed in parallel for each conjugate selected.

Additionally, the $ID_{50}$ level of the conjugate in question can be one of the dosage levels selected and the other two selected to reach a toxic level, and the lowest dose does not indicate a biologically demonstrable effect, e.g., destruction of the tumor, the toxicology tests should be repeated using appropriate new doses calculated on the basis of the results obtained. Young, healthy mice or rats belonging to a well-defined strain are the first choice of species, and the first studies use the intramuscular, the preferred, route of administration. Control groups given a placebo or being untreated are included in the tests. Tests for general toxicity as outlined above should normally be repeated in another non-rodent species, e.g., a rabbit or a dog.

Studies may also be repeated using other routes of administration.

Further single dose toxicity tests should be conducted in such a way that signs of acute toxicity are revealed and the mode of death determined. The dosage to be administered is calculated on the basis of the results obtained in the above-mentioned toxicity tests. It may be desired not to continue studying all of the initially selected conjugates. Data on single dose toxicity, e.g., $LD_{50}$, the dosage at which half of the experimental animals die, is to be expressed in units of weight or volume per kg of body weight and should generally be furnished for at least two species with different modes of administration. In addition to the $LD_{50}$ value in rodents, it is desirable to determine the highest tolerated dose and/or lowest lethal dose for other species, e.g., dog and rabbit.

When a suitable and presumably safe dosage level has been established as outlined above, studies on the drug's chronic toxicity, its effect on reproduction and potential mutagenicity may also be required in order to ensure that the calculated appropriate dosage range will be safe, also with regard to these hazards.

Pharmacological animal studies on pharmacokinetics revealing, e.g., absorption, distribution, biotransformation and excretion of the conjugate and metabolites are then to be performed. Using the results obtained, studies on human pharmacology are then designed. Studies of the pharmacodynamics and pharmacokinetics of the conjugates in humans should be performed in healthy subjects using the routes of administration intended for clinical use, and can be repeated in patients. Dose-response relationship when different doses are given, or when several conjugates are given together, should be studied in order to elucidate the dose-response relationship (dose vs. plasma concentration vs. effect), the therapeutic range and the optimum dose interval. Also, studies on time-effect relationship, e.g., studies into the time-course of the effect and studies on different organs in order to elucidate the desired and undesired pharmacological effects of the drug in particular on other viral organic systems should be performed.

The conjugate is then ready for clinical trials to compare the efficacy of the conjugate to exiting therapy. A dose-response relationship for therapeutic effect and for side effects can be more finely established here.

Besides intravenous administration, the acid form of the conjugates nay be administered by any means of parenteral administration. However, the free acid form of the glucuronides should not be administered orally, as it is known that β-glucuronidase is present in the digestive tract. The tri-acetylated conjugates, however, can be administered orally, as the β-glucuronidase in the digestive tract does not affect the acetylated conjugates.

The amount of conjugate to be administered to any given patient must be determined empirically and will differ depending upon the condition of the patient. Relatively small amounts of the conjugates can be administered at first, with steadily increasing dosages if no adverse effects are noted. Of course, the maximum safe toxicity dosage as determined in routine animal toxicity tests should never be exceeded.

Optimally, the concentration of conjugates to be administered should be sufficient to provide a concentration of approximately 0.05 to 10 mM of acetaminophen and, optionally, approximately $5 \times 10^{-4}$M to about $5 \times 10^{-3}$M of phenolic cytotoxic compound to the tumor site.

It is clear that any tumor cells having both tyrosinase activity and saccharidase activity as well as cytochrome p450 activity may be treatable in accordance with the present invention, with the remaining organs of the body being protected by the alkalinization step. Tumors which are known to have saccharidase activity include solid breast tumors and their metastases, bronchogenic carcinoma and its metastases, and lymphomas, as well as lung carcinoma including non-small cell carcinoma and squamous cell carcinoma, colon carcinoma, testicular carcinoma, hepatic carcinoma, pancreatic carcinoma, ovarian carcinoma, leukemia, bronchogenic carcinoma, prostate carcinoma and rectal carcinoma. Hodgkin's disease can also be treated by the method and composition of the present invention. Tumors which have high tyrosinase activity, as noted above, include melanoma, amelanotic melanoma, breast carcinoma, and bladder carcinoma, as well as a number of the other tumors noted above.

When it is desired to induce hypothermia to increase saccharidase activity, a method should be selected by which the temperature is raised as much as possible without risking damage to healthy portions of the body, such as the eyes. An increase of about 2° C. for whole body hypothermia, and as much as 4.5° C. for local hypothermia, is preferred. The hypothermia should be timed to last about one hour at the time of greatest saccharide concentration at the tumor site. For example, when local microwave treatment is selected, it should begin about one half hour after commencement of the intravenous conjugate drip and be continued for about one hour. The proper dosage of known pyrogens to achieve the desired degree of hypothermia would be known to those skilled in the art, and can be easily empirically determined without undue experimentation. A dosage of about 30 ng/day of dinitrophenol, for example, would be appropriate.

Because the triacetylated form of the conjugate is not affected by saccharidase in the digestive tract, this form of the conjugate can be administered orally without loss of activity. Moreover, it has been found that, because the triacetylated form of the conjugate is lipid soluble, it is retained in the body for a much longer time than the free acid form of the conjugate. The tri-acetylated form of the conjugate provides an additional level of protection for normal cells, as the cytochrome p450 substrate and the phenol compounds are not released in the body until the acetyl groups are removed and the saccharide is removed from the conjugate. Since primitive cells such as cancer cells produce acetylase, this acetylase removes the acetyl groups from the conjugate. The more anaplastic (i.e., more immature) the tumor cells, the more enzymes they produce, so that the triacetylated form of the drug is more selectively toxic to tumor cells than even the conjugated form. Thus, since two steps are required to liberate the phenolic compound, the conjugates are even more preferentially delivered to the site of an active tumor than are the acid form of the conjugates.

When estrogen or testosterone are administered, a dose of from about 3–15 mg/kg body weight/day provides the desired inducement to saccharidase activity.

To treat a patient suffering from a cancer which exhibits tyrosinase activity as well as saccharidase activity, the cytochrome p450 substrate conjugates and the optional phenolic conjugates are administered in the form of saccharide conjugates or acetylated saccharide conjugates. When administered in the form of saccharide conjugates per se, the conjugates must be administered parenterally. However, when administered as the acetylated conjugates, the conjugates can be administered orally, most conveniently in the form of capsules.

Capsules are formulated generally containing approximately 1 gram of cytochrome p450 substrate saccharide per capsule. When only conjugate of cytochrome p450 substrate is administered, the dosage is generally about five to ten capsules three times daily, providing about 15 to 30 grams of conjugate per day. The patient's serum is measured after a loading dosage of the conjugate is administered to maintain a level of approximately 1 mM of cytochrome p450 substrate conjugate in the serum.

When a combination of conjugates is administered, however, the number of capsules of each conjugate can be greatly decreased. For example, when a combination of a conjugate of acetaminophen and a conjugate of a cytotoxic phenol are administered, only from about two to five capsules, containing approximately 0.6 gram of each conjugate per capsule of combined active ingredients, need be administered three times daily. The amount of active ingredients in the serum need only be maintained at approximately 0.25 to about 0.5 mM of combined active ingredients.

As noted above, para-methoxyphenyl glucuronide is the preferred compound for use with cytochrome p450 substrate conjugates according to the present invention. This compound is preferred because it is particularly non-toxic to the non-cancerous cells. As with other saccharide compounds of the present invention, the para-methoxy-phenyl glucuronide can be used in either the triacetylated form or in the free acid form.

In the first step after administering cytochrome p450 substrate saccharide conjugate to a patient, the "prodrug" is hydrolyzed at the cancer site by the saccharidase to yield the cytochrome p450 substrate, e.g., acetaminophen. This reaction takes place only at the cancer site because only at the cancer site is the saccharidase enzyme available to catalyze the reaction. The acetaminophen that is released is then available as a substrate for the second reaction, which is oxidized by cytochrome p450 to yield N-acetyl benzoquinone imine, which is extremely toxic to cancer cells. N-acetyl benzoquinone imine has a strong affinity for sulfhydryl groups of proteins. As long as the affected cell possesses a reduced glutathione molecule available, the glutathione will be conjugated to the five site of the N-acetyl benzoquinone imine to produce mercapturic acid. This reaction proceeds until the glutathione molecule are depleted. Then the N-acetyl-benzoquinone imine will form covalent bonds in a non-reversible reaction with the thiol groups of the essential proteins, which causes necrosis and death of the cells.

When para-methoxy-phenyl or other cytotoxic phenol saccharide is administered along with the acetaminophen saccharide, the para-methoxy-phenyl saccharide prodrug is hydrolyzed at the cancer site by saccharidase at the tumor site to yield 4-hydroxy anisole. This reaction takes place only at the cancer site because only at the cancer site is the saccharidase enzyme available to catalyze the reaction. The 4-hydroxy anisole that is released is then available as a substrate for the second reaction, which is catalyzed by the enzyme tyrosinase. The tyrosinase oxidizes the 4-hydroxy anisole to methoxy-ortho-benzoquinone. The methoxy-ortho-benzoquinone is an unstable molecule that spontaneously reacts with water to release hydrogen peroxide. When the hydrogen peroxide reaches a certain concentration, living membranes can no longer cope with the oxidative damage produced thereby, and are destroyed. To enhance the oxidative damage in these cancerous cells, the hydrogen peroxide concentration is further increased by inhibiting the reducing enzyme glutathione reductase.

Para-methoxy phenol saccharide is particularly useful as an adjunct to acetaminophen saccharide conjugates because the para-methoxy-phenol saccharide prodrug becomes extremely toxic after two sequential steps of activation and potentiation, and concomitant inhibition of a third enzyme, glutathione reductase. This occurs via two sequential enzymatic systems that exist only at the malignant growth, i.e., saccharidase and tyrosinase.

The N-acetyl-benzoquinone imine also inhibits glutathione reductase by reacting with the thiol groups of glutathione reductase. However, this reaction is not important any more because once the glutathione is reacting with N-acetyl-benzoquinone imine the glutathione reductase cannot react with it anymore since the glutathione is the first to be irreversibly inactivated and removed by the N-acetyl benzoquinone imine as a mercapturic acid. Thus, the presence or absence of glutathione reductase or peroxidase is not important, so by administering PAPG there is no need to inhibit these enzymes.

Because the conjugates of the present invention are saccharides, they are hydrolyzed by the saccharidase produced by tumor cells to release the active form of the compound at the site of the tumor. The pH for optimal enzymatic activity for most saccharides is about 5.5, so that acidification of the tumor is desirable. This acidification of the tumor, as described elsewhere in this specification, can be achieved by administering glucose to the patient thirty minutes prior to the treatment, as orally administered glucose expresses itself in acidification of the tumor due to accumulation of lactic acid. Of course, if the prodrug conjugate used is a glucose conjugate, an acidification compound other than glucose is administered.

In a preferred treatment protocol, the patient is preferably on a maintenance dosage of a corticosteroid, such as 4 mg of dexamethasone, throughout the duration of the treatment. This dosage ensures delay in premature fibrotic changes and interference with the blood and drug supply to the tumor. Of course, any of the conventional corticosteroids can be used for this purpose.

It should be noted that corticosteroids inhibit the production of tumor necrosis factor, and thus reduce the malaise, loss of appetite, and cachexia that accompany malignant diseases. In addition, corticosteroids help in maintaining high levels of blood glucose, and for brain tumors, a higher dosage is useful. Omeprazole, Zantac, Cimetidine or other anti-ulcer drugs should also be administered concomitantly to prevent ulcers, since corticosteroids are known to induce ulcers. During therapy according to the present invention, no vitamin C supplementation or any ascorbate should be administered to the patient. Ascorbates, being antioxidants, protect the malignant cells from the oxidative damage caused by the metabolites of the cytotoxic phenolic compounds when these latter compounds are used as adjuncts to the acetaminophen conjugates. Any vitamin E administered also acts as an antioxidant, and reduces the tyrosinase.

Additionally, during therapy no compounds should be administered which are substrates for the enzyme of the tumor sought to be used for acting on the conjugate administered. For example, if the conjugate used is a conjugate with galactose, the patient should avoid galactose-containing foods. Likewise, where glucose is the conjugate, glucose-containing foods should be avoided.

The phenolic conjugates to be used in conjunction with cytochrome p450 substrate conjugates according to the present invention can be administered in combination along with cytochrome p450 substrate conjugates to patients suffering from tyrosinase-dependent cancers at doses ranging from about 0.5–30 grams/day of total dosage. Although it has been found that maintaining a serum level of about 0.5 to 1 mM of conjugate is desirable, serum levels ranging from about 0.05 to about 10 mM can be used, depending upon the patient's response to the treatment. As noted above, one skilled in the art can readily ascertain what saccharide or saccharides should be used to prepare conjugates to treat a particular tumor, and can tailor the prodrugs accordingly. As noted above, synergistic effects are obtained by combining conjugates. Some of these synergistic combinations include conjugates of β-glucuronides with galactosides for treating mammary tumors, and α-glycosides with β-glucuronides for treating melanomas. Determinations of preferred combinations for each tumor type is well within the skill of the art.

The conjugates can be incorporated in any conventional solid or liquid pharmaceutical formulation in any concentration desired. For example, injectable compositions, composition which may be adsorbed through the mucosa, or transdermally administrable solutions may be used. The pharmaceutical formulations of the invention comprise an effective amount of the conjugates or their analytes.

In addition to the pharmacologically active conjugates, the new pharmaceutical preparations may contain suitable pharmaceutically acceptable carriers comprising excipients and auxiliaries which facilitate processing of the conjugates into preparations which can be used pharmaceutically. These compositions, such as suppositories for rectal administration, as well as suitable solutions for administration by injection or be parental administration, contain from about 0.01 to 99 percent, preferably from about 20 to 75 percent, of active compound, together with the excipient.

Pharmaceutical preparations which can be used rectally include, for example, suppositories which consists of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parental administration include aqueous solutions of lactose or of a combination of lactose and a water-soluble form of the conjugate. In addition, suspensions of the active compounds as appropriate oily injection suspensions may also be administered. Suitable lipophilic solvents or vehicles include fatty oils, such as sesame oil, or synthetic fatty acid esters, such as ethyl oleate or triglycerides. Aqueous injection suspension that may contain substances which increase the viscosity of the suspension include sodium carboxymethyl cellulose, sorbitol, and/or dextran.

Administration may be parental, subcutaneous, intravenous, intramuscular, intraperitoneal, or transdermal routes. As noted above, the dosage administered will be dependent upon the age, health, and weight of the recipient, type of concurrent treatment, if any, frequency of treatment, and the nature of the effect desired.

Each formulation according to the present invention may additionally comprise inert constituents including pharmaceutically acceptable carriers, diluents, fillers, salts and other materials well known to the art, the selection of which depends on the dosage form used, the particular purpose to be achieved according to the determination of the ordinary skilled artisan in the field, and the properties of such additives. Examples of carriers and diluents include carbohydrates, lipids and water.

The conjugates of the present invention can be combined with a pharmaceutically acceptable carrier therefore, and optionally other therapeutic and/or prophylactic ingredients. The carriers must be "acceptable" in the sense of being compatible with the other ingredient of the formulation, and not deleterious to the recipient thereof.

Pharmaceutical formulations suitable for oral administration of the conjugates wherein the carrier is a solid are most preferably presented as unit dose formulations such as boluses, capsules, and the like, as well as sachets or table, each containing a predetermined amount of active ingredient. A tablet may be made by compression or molding, optionally with one or more accessory ingredients. Compressed tablets may be prepared by compressing in a suitable machine the active conjugate of mixture of active conjugates in a free-flowing form, such as powder or granules, optionally mixed with a binder, lubricant, interdiluent, lubricating, surface active or dispersing agent. Molded tablets may be made by molding the active conjugate with an inert liquid diluent. Tablets may be optionally coated and, if uncoated, may optionally be scored. Capsules may be prepared by filling the active conjugate, either alone or in admixture with another conjugate and/or with one or more accessory ingredients, into the capsule cases and then sealing them in the usual manner. Sachets are analogous to capsules, wherein the active conjugate or conjugates, together with any optional accessory ingredients, are sealed in a rice paper envelope.

Pharmaceutical formulations suitable for oral administration of the conjugates in which the carrier is a liquid may conveniently be presented as a solution in a pharmaceutically acceptable solvent which is inert to the conjugates included therein.

Pharmaceutical formulations suitable for parenteral administration are conveniently presented in unit dose or multidose containers which are sealed after introduction of the formulation unit required for use.

It should be understood that in addition to the aforementioned carrier ingredients, the pharmaceutical formulations described above may include, as appropriate, one or more additional carrier ingredients such as diluents, buffers, lubricants, preservatives and the like, and substances included for the purpose of rendering the formulation isotonic with the blood of the intended recipient.

The pharmaceutical formulations may be formulations in which the active compound or compounds may be administered, and include those suitable for oral or parenteral (including intramuscular and intravenous) administration. The formulations may, where appropriate, be conveniently presented in discrete dosage units and may be prepared by any of the methods known in the art of pharmacy. All of the methods include the step of bringing into association the active compound with liquid carriers of finely divided solid carrier, or both, and then, if necessary, shaping the product into the desired formulation.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein are for the purpose of description and not of limitation.

What is claimed is:

1. A method for selectively treating tumor cells which have saccharidase activity comprising administering to a patient afflicted with a malignant tumor an effective amount of a saccharide conjugate of a substrate for cytochrome p450 which after oxidation by cytochrome p450, reacts with thiol groups, or a pharmaceutically acceptable ester or salt thereof.

2. The method according to claim 1 wherein the substrate for cytochrome p450 is selected from the group consisting of acetaminophen, glutathione and ornithine decarboxylase.

3. A method for selectively treating tumor cells which have both saccharidase activity and tyrosinase activity comprising an effective amount of a saccharide conjugate of a substrate for cytochrome p450 which, after oxidation by cytochrome p450, reacts with thiol groups or a pharmaceutically acceptable ester or salt thereof in combination with an effective amount of at least one conjugate made by conjugating a saccharide or a pharmaceutically acceptable ester or salt thereof to a cytotoxic phenolic compound which is also a substrate for tyrosinase.

4. The method according to claim 2 wherein at least one of the saccharide conjugates is formed from the triacetylated form or the heptacetylated form of the saccharide.

5. The method according to claim 3 wherein the at least one conjugate is administered orally.

6. The method according to claim 2 wherein the cytotoxic phenolic compound is selected from the group consisting of 4-hydroxyanisole, L-3,4-dihydroxyphenylalanine, dopamine, tert-butylcatechol, hydroquinone, 6-hydroxydopa, 4-tert-butyl phenol, 7-hydroxy coumarin, 4-tert-amyl phenol, 4-benzomethoxy phenol and methyl gallate.

7. The method according to claim 5 wherein the cytotoxic compound is 4-hydroxyanisole.

8. The method according to claim 2 wherein the substrate for cytochrome p450 is selected from the group consisting of acetaminophen, glutathione, and ornithine decarboxylase.

9. The method according to claim 1 wherein the saccharide is selected from the group consisting of glucuronides, glucose, galactose, fructose, arabinose, mannose, gulose, ribose, xylose, lyxose, erythrose, maltose, cellobiose, lactose, sucrose, N-acetylglucosamine, N-acetylgalactosamine, rhamnose and mixtures thereof.

10. A composition for selectively treating tumor cells which have both saccharidase activity and tyrosinase activity comprising an effective amount of a saccharide conjugate of a substrate for cytochrome p450 which, after oxidation by cytochrome p450, reacts with thiol groups or a pharmaceutically acceptable ester or salt thereof and an effective amount of at least one conjugate made by conjugating a saccharide or a pharmaceutically acceptable ester or salt thereof to a cytotoxic phenolic compound which is also a substrate for tyrosinase.

11. The composition according to claim 10 wherein the substrate for cytochrome p450 is selected from the group consisting of acetaminophen, ornithine decarboxylase, and glutathione.

12. The composition according to claim 11 wherein at least one of the saccharide conjugates is formed from the triacetylated form or the heptacetylated form of the saccharide.

13. The composition method according to claim 12 including an orally acceptable pharmaceutical carrier.

14. The composition according to claim 11 wherein the cytotoxic phenolic compound is selected from the group consisting of 4-hydroxyanisole, L-3,4-dihydroxyphenylalanine, dopamine, tert-butylcatechol, hydroquinone, 6-hydroxydopa, 4-tert-butyl phenol, 7-hydroxy coumarin, 4-tert-amyl phenol, 4-benzomethoxy phenol and methyl gallate.

15. The composition according to claim 14 wherein the cytotoxic compound is 4-hydroxyanisole.

16. The composition method according to claim 11 wherein the saccharide is selected from the group consisting of glucuronides, glucose, galactose, fructose, arabinose, mannose, gulose, ribose, xylose, lyxose, erythrose, maltose, cellobiose, lactose, sucrose, N-acetylglucosamine, N-acetylgalactosamine, rhamnose and mixtures thereof.

17. The method according to claim 1 wherein the tumor cells are selected from the group consisting of solid breast tumors, lung carcinomas, colon carcinoma, testicular carcinoma, hepatic carcinoma, pancreatic carcinoma, ovarian carcinoma, bronchogenic carcinoma, prostate carcinoma, and rectal carcinoma.

* * * * *